United States Patent [19]

Blay

[11] 4,214,050
[45] Jul. 22, 1980

[54] PREVENTION OF ELECTRODE FOULING

[75] Inventor: George A. Blay, Corpus Christi, Tex.

[73] Assignee: Celanese Corporation, New York, N.Y.

[21] Appl. No.: 957,947

[22] Filed: Nov. 6, 1978

[51] Int. Cl.$^2$ ............................................. C12Q 1/29
[52] U.S. Cl. ................................... 435/29; 424/130; 424/245; 422/28
[58] Field of Search ..................... 435/4, 29, 243, 262, 435/317, 801, 813, 817; 134/26; 422/28

[56] References Cited

U.S. PATENT DOCUMENTS 3,344,061  9/1967  Kellum ........................ 422/28 X

OTHER PUBLICATIONS

Polymetron Brochure, "Industrial pH and Redox Measurement with Automatic Self-Cleaning of the Electrodes", Division of Uster Corp.

*Primary Examiner*—Robert J. Warden

[57] ABSTRACT

The fouling of electrodes of pH meters used in anaerobic bacteria digestion processes may be prevented by intermittently immersing the electrodes in an aqueous bactericidal solution, which bactericidal solution is preferably buffered to a known pH. While immersed in such a buffered bactericidal solution, there is simultaneously accomplished the killing of the bacteria accumulated on the electrode and the calibration of the pH meter.

22 Claims, No Drawings

PREVENTION OF ELECTRODE FOULING

BACKGROUND OF THE INVENTION

The present invention relates to the prevention of fouling of electrodes used to measure or monitor the pH of the bacteria-containing liquid of an anaerobic digestion process.

Many processes are in use today wherein the decomposition of organic molecules is accomplished through the use of anaerobic bacteria. Such processes are known by various names such as bioconversion processes, anaerobic decomposition processes, anaerobic digestion processes, anaerobic filters, anerobic reactors, and the like. Herein, the term "anaerobic digestion process" will be applied to these processes wherein anaerobic bacteria decompose organic molecules to mainly carbon dioxide and methane. These anaerobic digestion processes are utilized for various purposes, in some cases the primary function or desired result being the decomposition of an organic molecule which itself presents a disposal problem; while in some cases the primary function is the production of methane as an energy source.

In an anaerobic digestion process, generally two different bacteria populations live in balance, one group being known as the acid formers, and one group known as the methane formers. The acid formers decompose relatively large molecules to small $C_1$–$C_4$ organic compounds such as formic acid, acetic acid, propionic acid and butyric acid. The methane formers then further decompose the $C_1$–$C_4$ molecules into carbon dioxide and methane. The anaerobic bacteria known as the methane formers are especially delicate and sensitive to pH, and the pH of a liquid in which an anaerobic digestion process takes place must remain within a narrow range of about 5 to 8, more usually within the range of about 6.2 to 7.5, in order to prevent killing of the bacteria.

Due to the sensitivity of an anaerobic digestion process to pH, the pH of the anaerobic bacteria-containing liquid of the process is generally measured or monitored on a continuous or frequent intermittent basis in order that any adverse change in pH may be detected and corrected. This is accomplished through use of a pH meter or other pH measuring device having electrodes which are immersed in the bacteria-containing liquid. Usually a small sample side-stream of the liquid from the main anaerobic reactor is passed through a cell or chamber housing the electrodes such that the electrodes (the sensing areas thereof) are immersed in the liquid flowing through the chamber. The sample side-stream is then generally discarded in a large commercial process, but may be returned to the reactor in a small laboratory or pilot plant operation.

A problem arises in the pH measurement of the bacteria-containing liquid because the bacteria in the liquid very quickly cause a gel-type film to form and grow on the surface of the sensing membrane of the pH glass electrode, and on the porous plug of the reference electrode. This film causes an increased electrical resistance which results in an inaccurate pH measurement. The inaccuracy in the pH measurement is frequently termed as "drift". In a typical anaerobic digestion process the film buildup will require electrode replacement after only two or three days of operation.

Various techniques have been devised for cleaning of pH electrodes used in other processes. These cleaning systems, which are commercially available, include mechanical systems wherein a brush or scraper physically removes fouling; chemical spray systems wherein an acid, base or emulsifier is periodically sprayed on to the electrode; hydrodynamic systems wherein turbulence is induced in the sample flow to effect cleaning through abrasive action of suspended solids contained in the sample flow; and acoustical systems wherein cleaning is accomplished through use of ultrasonic waves. None of the prior art systems provide effective cleaning of the gel-type film caused by anaerobic bacteria. For example, the brushes and scrapers of a mechanical system will not clean the pores of the porous plug of the reference electrode; and the chemical spray system appears to be mainly effective for prevention of inorganic deposits instead of those induced by the anaerobic bacteria. Ultrasonics and hydrodynamics have also been found to be unsatisfactory.

It is thus an object of the present invention to provide a new and effective method or system for prevention of fouling of pH electrodes used in an anaerobic digestion process. It is an additional object of the present invention to provide a method or system for periodic removal of the film on pH electrodes caused by anaerobic bacteria of an anaerobic digestion process. It is a further and additional object of the present invention to provide a method for intermittent treating of pH electrodes used in an anaerobic digestion process, and which method allows calibration of the pH measuring device during the treating. Additional objects will become apparent from the following description of the present invention.

SUMMARY

The foregoing and additional objects are accomplished by the present invention which in one of its aspects is, in a process wherein the pH of the anaerobic bacteria-containing liquid of a continuous anaerobic digestion process is monitored by means of a pH measuring device containing electrodes which are immersed in said bacteria-containing liquid in order to obtain a measurement of the pH of said bacteria-containing liquid, said electrodes comprising a reference electrode and a glass electrode, and wherein anaerobic bacteria decompose organic molecules so as to produce a product of mainly carbon dioxide and methane, the improvement which comprises cyclically immersing said electrodes in said bacteria-containing liquid and in a bactericidal solution so as to prevent fouling of said electrodes, each cycle comprising a first time period during which said electrodes are immersed in said bacteria-containing liquid in order to measure the pH thereof and a second time period during which said electrodes are immersed in said bactericidal solution, the time ratio of said first time period to said second time period being no greater than about 10:1, said first time period of said cycle during which said electrodes are immersed in said bacteria-containing liquid not exceeding about ten hours in duration, said bactericidal solution containing a bactericide which is effective in killing said anaerobic bacteria, and said bactericidal solution containing an amount of said bactericide effective to kill the anaerobic bacteria remaining on the said electrodes after their having been immersed in the said bacteria-containing liquid.

DETAILED DESCRIPTION OF THE INVENTION

It has been found that film buildup on pH electrodes utilized in an anaerobic digestion process can be prevented if the electrodes are periodically withdrawn from contact with the bacteria-containing liquid and immersed in an aqueous bactericidal solution. The bactericide used should of course be one which is effective in killing the anaerobic bacteria present; however, the present invention does not reside in the discovery of a new bactericide and any of numerous bactericides available can accomplish the desired bactericidal action. Two preferred bactericides are hydrogen peroxide and phenyl mercuric acetate. The amount of bactericide in the aqueous solution need only be sufficient to kill the bacteria which resides or remains on the pH electrodes after they have been immersed in the anaerobic bacteria-containing liquid. This effective amount will vary from bactericide to bactericide but can be readily determined by one skilled in the art without any undue experimentation.

When using phenyl mercuric acetate, only about 10 to 50 p.p.m. (parts per million) by weight are needed in the aqueous solution to provide the desired bactericidal action; and when using hydrogen peroxide at least about 0.1% by weight, preferably 0.2% to 4.0% by weight, of hydrogen peroxide is needed. Hydrogen peroxide is most preferred as a bactericide because its disposal presents less environmental problems.

When using hydrogen peroxide as the bactericide, it will be beneficial to add a complexing agent to the aqueous solution in order to complex any alkaline earth metals or transition metals present because these metals catalyze the decomposition of hydrogen peroxide. If a high purity water is used in forming the aqueous bactericidal solution these metals will probably not be present to any appreciable extent; however, it will be most convenient to use tap water in forming the aqueous bactericidal solutions, and tap water will generally contain these metals. The amount of any complexing agent should be that amount sufficient to complex the transition and alkaline earth metals present which will vary from water source to water source. The preferred complexing agent is ethylenediaminotetraacetic acid (hereafter referred to as EDTA), and at least about one mole of EDTA per atom of metal present should be utilized. An alkaline salt of EDTA may be used.

Another agent which is desirably present in the aqueous bactericidal solution is a non-ionic detergent which will aid in preventing the formation of a grease or oil film on the electrodes. The detergent is desirably present in the aqueous bactericidal solution in an amount within the range of about 0.02% to 5.0% by weight, depending largely on the particular non-ionic detergent used. Suitable non-ionic detergents include isooctyl phenoxy polyethoxy ethanol, octylphenyl polyethoxy ethanol and nonylphenoxy polyethoxy ethanol.

Although not necessary for the bactericidal action, a buffer is desirably present in the bactericidal solution. The buffer should be of such a type and present in sufficient amounts to cause the pH of the bactericidal solution to be maintained at a substantially constant pH which is within the range of about 5 to 8, preferably 6 to 8. The presence of a buffer is desired because it allows the pH measuring device to be calibrated during the time of electrodes are immersed in the bactericidal solution. This is important due to the great significance of a pH error of as little as 0.1 pH to the performance of the anerobic process. According to the present invention, the pH electrodes will be alternately immersed in the bacteria-containing liquid and the bactericidal solution; and, since a bactericidal solution of know pH is used, the pH meter reading can be observed during the bactericidal solution immersion period and compared to the known pH of the bactericidal solution. If the pH meter reading varies from the known pH of the bactericidal solution, the operation will know that "drift" is occurring and that recalibration of the instrument is necessary to obtain accurate measurement.

Any of the conventional buffers may be used although the phosphate buffers are preferred. For example mixing of monosodium phosphate and disodium phosphate to obtain the desired pH will provide good results, as will mixing phosphoric acid and sodium hydroxide. Only a small concentration of the buffers is generally necessary to cause the pH of the bactericidal solution to be maintained within the desired range. Generally from about 0.05 to 0.25 moles per liter of the buffer will be sufficient. The aqueous bactericidal solution contained in the bactericide and the buffer, and any other components such as a non-ionic detergent, should generally contain at least 50% by weight of water.

The desired pH of the aqueous bactericidal solution should be adjusted by use of the buffer to a pH within the range of about 5 to 8, preferably within the range of about 6 to 8. The pH range of 6 to 8 is preferred for two reasons. First, the anaerobic bacteria of the anaerobic digestion process cannot normally survive outside this range and the pH monitoring equipment utilized will thus normally read only within this narrow range. Since one function of the bactericidal solution is to allow calibration of the pH monitoring equipment, the pH of the bactericidal solution must therefore be within the measurable range of the pH measuring equipment.

A second reason for having the pH of the bactericidal solution within the range of 6 to 8 is to prevent a large kill of the anaerobic bacteria in the anaerobic digester in the event of an accidental spill or leakage of the bactericidal solution into the digester. In the event of such a leakage or spill, some kill of the anaerobic bacteria would in any event take place due to the bactericide present; however, the kill would be much larger if the pH of the bactericidal solution were outside the range of 6 to 8.

It is especially preferred that the pH of the aqueous bactericidal solution be buffered to a pH of less than 7, for example within the range of 6 to 7. The reason for maintaining a pH of less than 7 is to prevent the formation of inorganic deposits such as calcium carbonate. In addition to the above-mentioned buffers, other suitable buffers include proper mixtures 0.2 M boric acid, 0.05 M citric acid, with 0.1 M trisodiumphosphate; or mixtures of 0.1 M citric acid with 0.2 M disodium phosphate; or mixtures of 0.2 M potassium biphthalate with 0.2 M sodium hydroxide; or glycerophosphoric acid with an alkaline base; or EDTA with an alkaline base.

Operating in accordance with the present invention will be cyclic in nature, with the measurement of the pH of the bacteria-containing liquid being intermittent. Each cycle will contain a first determinate time period of no greater than 10 hours in duration in which the pH of the bacteria-containing liquid will be measured. This can be accomplished by continuously withdrawing a sample portion of the bacteria-containing liquid from the anaerobic digester, and passing the liquid through a cell or chamber into which extends the electrodes of the pH measuring device. The electrodes are immersed in the bacteria-containing liquid as it passes through the electrode chamber, and the pH of the liquid continuously measured or monitored during this period. The sample stream of bacteria-containing liquid exiting the chamber should generally be discarded and not returned through the anaerobic digester. The sample may be returned to the anaerobic digester but such a return of sample allows a greater chance of some of the bactericidal solution leaking or otherwise accidentally spilling into the anaerobic digester. In laboratory or pilot plant operation the return of sample is, however, usually necessary because the sample volume is usually relatively large compared to the total volume of liquid in the anaerobic digester. The length of the period during which the pH of the bacteria-containing liquid is monitored each cycle should not exceed 10 hours, and for example may be a period from about 5 minutes to 10 hours. If the electrodes remain immersed in the bacteria containing liquid for a time subtantially in excess of 10 hours, the film caused by the bacteria is generally not readily removable by the bactericidal solution. A time period having a length within the range of about 10 minutes to 5 hours is preferable.

Each cycle will also have a determinate time period during which the electrodes will be immersed in the bactericidal solution. This can readily be accomplished by filling or charging the electrode chamber with a batch of bactericidal solution and allowing this batch to remain in the chamber for the desired length of time. Each batch should be discarded after use.

The time period during which the electrodes are immersed in the bactericidal solution can immediately follow the period during which the electrodes are immersed in the sample flow; however, it is recommended that the electrodes and the electrode chamber be flushed with water between the time the electrodes are immersed in the bacteria-containing liquid and the time the electrodes are immersed in the bactericidal solution. The water flush needs only be of short duration of, for example within the range of 10 seconds to 30 minutes, preferably 10 seconds to 5 minutes. The water flush can be accomplished by merely filling the electrode chamber with a batch of water and draining it, or preferably by continuously flowing water through the chamber for the desired period of time.

The length of the time period of each cycle in which the electrodes remain immersed in the bactericidal solution will depend somewhat on the length of time the electrodes have been immersed in the bacteria-containing liquid. The longer the immersion in the bacteria-containing liquid, the greater the film build-up and the greater is the difficulty of removal. Generally the time ratio of the length of the period during which the electrodes are immersed in the bacteria-containing liquid to the length of the period during which the electrodes are immersed in the bactericidal solution should be no greater than 10:1 and is preferably within the range of about 1:20 to 10:1, especially within the range of about 1:3 to 3:1. Satisfactory results have been accomplished with cycles of about one hour in length, each cycle comprising a first 20 minute period during which the pH of a sample was monitored, followed by a 1 minute period during which the pH chamber was flushed with water, and a 39 minute period during which the chamber was filled with a bactericidal solution. In order to extend the electrode life as long as possible, the time in which the electrodes are immersed in the bacteria-containing liquid should be kept to a minimum. In some processes the monitoring of pH for 10 minutes each hour might provide sufficient control, while in other processes which are subject to more rapid changes in pH it might be necessary to monitor pH as much as 50 minutes out of each hour.

The following example is given to illustrate the invention, but should not be construed as limiting the scope thereof.

EXAMPLE

An aqueous bactericidal solution was prepared which contained, in addition to the water, about 400 p.p.m. (parts per million by weight) of the disodium salt of EDTA as a complexing agent, about 0.7% by weight of hydrogen peroxide bactericide and 0.05% by weight of Triton X-100 detergent (such being an isooctyl phenoxy polyethoxy ethanol manufactured by Rohm & Haas Company). Additionally, to the bactericidal solution there was added a sufficient amount of 0.2 M phosphate buffer (made from a mixture of solutions of phosphoric acid and sodium hydroxide) to adjust the pH to 6.2.

The bactericidal solution was used in the intermittent monitoring of the pH of the anaerobic bacteria-containing liquid of a continuous anaerobic digestion process conducted in a laboratory apparatus. The pH monitoring was accomplished by cyclically repeating the sequential steps of: (1) for a period of 18 minutes continuously withdrawing the sample portion of the process liquid and passing it through a chamber into which extended the electrodes of a pH meter such that the electrodes were immersed in the process liquid as it flowed through the chamber, the process liquid being returned to the anaerobic digestion process after passing through the chamber; followed by (2) flushing the chamber and the electrodes with water for a period of 2 minutes by continuously passing water through the chamber, the wash water being discarded after passing through the chamber; followed by (3) filling the chambers with a batch of bactericidal solution and holding the batch of bactericidal solution in the chamber for a period of 38 minutes, the electrodes being immersed in the bactericidal solution during such 38 minutes, the batch of bactericidal solution being discarded after use; followed by (4) again flushing the chamber and the electrodes with water for a period of 2 minutes by continuously passing water through the chamber, the wash water being discarded after passing through the chamber. Following step (4), steps (1) through (4) were again repeated and so forth and so on. During step (1) while the process liquid was passing through the chamber, the pH of the liquid was continuously measured and recorded. During step (3) while the bactericidal solution was in the chamber, the pH was measured and the pH reading compared against the known pH of 6.2; and, if the pH reading varied from 6.2 the instrument was recalibrated.

By operating accordingly a buildup of film on the electrodes was prevented and the electrodes lasted in excess of eight months without needing replacement. Without use of the bactericidal solution, it had been observed that undue electrode fouling occurred, usually within a few days.

The embodiments of the invention in which an exclusive right or privilege is claimed are defined as follows:

1. In a process wherein the pH of the anaerobic bacteria-containing liquid of a continuous anaerobic digestion process is monitored by means of a pH measuring device containing electrodes which are immersed in said bacteria-containing liquid in order to obtain a measurement of the pH of said bacteria-containing liquid, said electrodes comprising a reference electrode and a glass electrode, said anaerobic digestion process being one wherein the anaerobic bacteria of said bacteria-containing liquid decompose organic molecules to mainly carbon dioxide and methane, the improvement which comprises cyclically immersing said electrodes in said bacteria-containing liquid and in a bactericidal solution so as to prevent fouling of said electrodes, each cycle comprising a first time period during which said electrodes are immersed in said bacteria-containing liquid in order to measure the pH thereof and a second time period during which said electrodes are immersed in said bactericidal solution, the time ratio of said first time period to said second time period being no greater than about 10:1, said first time period of said cycle during which said electrodes are immersed in said bacteria-containing liquid not exceeding about ten hours in duration, said bactericidal solution containing a bactericide which is effective in killing said anaerobic bacteria, and said bactericidal solution containing an amount of said bactericide effective to kill the anaerobic bacteria remaining on the said electrodes after their having been immersed in the said bacteria-containing liquid.

2. The process of claim 1 wherein the said bactericidal solution is an aqueous bactericidal solution.

3. The process of claim 2 wherein the said time ratio is within the range of about 1:20 to 10:1.

4. The process of claim 2 wherein the said time ratio is within the range of about 1:3 to 3:1.

5. The process of claim 2 wherein said first time period of each said cycle during which said electrodes are immersed in said bacteria-containing liquid does not exceed about 5 hours in duration.

6. The process of claim 2 wherein said bactericidal solution contains in addition to said bactericide, from about 0.02% to 5.0% by weight of a non-ionic detergent.

7. The process of claim 2 wherein said bactericidal solution contains, in addition to said bactericide, a buffer of a type and in sufficient quantity to cause the said bactericide solution to be maintained at a substantially constant pH within the range of about 5 to 8.

8. The process of claim 2 wherein said bactericide is hydrogen peroxide, said hydrogen peroxide being present in said bactericidal solution in amounts from about 0.2% to 4.0% by weight.

9. The process of claim 8 wherein said bactericidal solution contains an amount of ethylenediaminotetraacetic acid, or salt thereof, sufficient to complex any alkaline earth metals and transition metals present in the said bactericidal solution.

10. The process of claim 2 wherein said bactericide is phenyl mercuric acetate.

11. The process of claim 2 wherein said electrodes are flushed with water between said first time period and said second time period of each said cycle.

12. The process of claim 1 wherein said bactericidal solution is an aqueous bactericidal solution which contains, in addition to said bactericide, a buffer of a type and in sufficient quantities to cause the said bactericidal solution to be maintained at a substantially constant pH which is within the range of about 6 to 8, and wherein the said time ratio is within the range of about 1:20 to 10:1, and wherein the said first time period during said cycle does not exceed about 5 hours in duration.

13. The process of claim 12 wherein said bactericidal solution contains from about 0.02% to 5.0% by weight of a non-ionic detergent.

14. The process of claim 12 wherein said bactericide is hydrogen peroxide, said hydrogen peroxide being present in said bactericidal solution in amounts from about 0.2% to 4.0% by weight.

15. The process of claim 14 wherein said bactericidal solution contains an amount of ethylenediaminotetraacetic acid, or alkaline salt thereof, sufficient to complex any alkaline earth metals and transition metals present in the said bactericidal solution.

16. The process of claim 15 wherein said bactericidal solution contains from about 0.02% to 5.0% by weight of a non-ionic detergent.

17. The process of claim 15 wherein said electrodes are flushed with water between said first time period and said second time period of each said cycle.

18. The process of claim 12 wherein said bactericide is phenyl mercuric acetate.

19. The process of claim 18 wherein said bactericidal solution contains from 0.02% to 5.0% by weight of a non-ionic detergent.

20. The process of claim 18 wherein said electrodes are flushed with water between said first time period and said second time period of each said cycle.

21. The process of claim 12 wherein said electrodes are flushed with water between said first time period and said second time period of each said cycle.

22. A method for intermittently monitoring the pH of the anaerobic bacteria-containing liquid of a continuous anaerobic digestion process, said method comprising cyclically repeating the sequential steps of:

(a) during a first determinate time period of no greater than ten hours, continuously withdrawing a sample portion of said bacteria-containing liquid from said anaerobic digestion process and continuously passing said sample portion through a chamber into which chamber extends the electrodes of a pH measuring device, such that said electrodes are immersed in said sample portion while said sample portion flows through said chamber, and continuously measuring the pH of said sample portion as it flows through said chamber;

(b) during a second determinate time period of at least 10 seconds but less than 30 minutes, continuously passing water through said chamber such that said electrodes are immersed in said water while said water flows through said chamber, such that said chamber and said electrodes are flushed with water;

(c) during a third determinate time period filling said chamber with a batch of an aqueous bactericidal solution such that said electrodes are immersed in said aqueous bactericidal solution during such third determinate time period, said aqueous bactericidal solution containing an effective amount of a bactericide which kills said anaerobic bacteria, said aqueous bactericidal solution also containing a buffer to maintain said aqueous bactericidal solution at a substantially constant pH which is within the range of 6 to 8, and continuously measuring the pH of said aqueous bactericidal solution during the time said electrodes are immersed therein, the ratio of the length of said first determinate time period to the length of said third determinate time period being within the range of 1:20 to 10:1.

* * * * *